(12) United States Patent
Fassina et al.

(10) Patent No.: US 6,222,011 B1
(45) Date of Patent: Apr. 24, 2001

(54) ANTIGENIC PEPTIDES

(75) Inventors: Giorgio Fassina, Milan; Antonio Verdoliva, Castellammare Di Stabia; Menotti Ruvo, Trevico, all of (IT)

(73) Assignee: Tecnogen S.C.p.A., Verna (IT)

( * ) Notice: Subject to any disclaimer, the term of this patent is extended or adjusted under 35 U.S.C. 154(b) by 0 days.

(21) Appl. No.: 09/177,595

(22) Filed: Oct. 23, 1998

Related U.S. Application Data

(63) Continuation of application No. 08/763,302, filed on Dec. 10, 1996, now Pat. No. 5,932,692.

(30) Foreign Application Priority Data

Dec. 11, 1995 (IT) .............................................. MI95A2582

(51) Int. Cl.$^7$ .................................................. A61K 38/00
(52) U.S. Cl. .......................... 530/300; 530/331; 530/324; 530/350
(58) Field of Search .............................. 436/543, 86, 161; 435/325, 326, 339.1, 346; 530/300, 333, 324, 331, 350, 388.1, 388.2, 388.22–389.2, 806; 424/184.1, 185.1, 186.1, 188.1, 204.1, 208.1

(56) References Cited

U.S. PATENT DOCUMENTS 5,470,955 11/1995 Craig .

5,932,692 * 8/1999 Fassina et al. ........................ 530/300

FOREIGN PATENT DOCUMENTS

| WO94 05311 | 3/1994 | (WO) . |
| WO 9523166 | 8/1995 | (WO) . |
| WO95 28497 | 10/1995 | (WO) . |

OTHER PUBLICATIONS

J. Biol. Chem. (1995), 30422 270 (51), –7 Coden: JBCHA3;ISSN: 0021–9248, Dec. 22, 1995, XP002017402 Verdoliva, Antonio et al: "Topological mimicry of cross–reacting enantiomeric peptide antigens".
Ezzell NIH Research vol. 7 p. 46 (1/95).
Spitler, Cancer Biotherapy, vol. 10 p. 1 (1995).
Haynes, Science vol. 260 p.1279 (5/93).
Verdoliva, et al "Topological Mimicry of Cross–Reacting Enantiomeric Peptide Antigens", J. Biol. Chem., 270(51), 30422–7 Coden: JBCHA3;ISSN: 0021–9258, Dec. 22, 1995, XP0002017402, pp. 57–62.
Stedman's Medical Dictionary 24th Edition p. 88–89 (1989).
Kikumoto et al Hybridoma vol. 14 p. 45 (2/95).
Lise et al, Peptide Research vol. 2, p114 (1989).
Ikagawa et al J Allergy Clin Immunol vol. 97 p 53 (1/96).
Cohen Science vol. 262 p. 980 (1993).

* cited by examiner

*Primary Examiner*—Sheela Huff
(74) *Attorney, Agent, or Firm*—Nixon & Vanderhye P.C.

(57) ABSTRACT

An improved antigenic peptide where the amino acid sequence is modified by replacing one or more amino acids with glycine.

**1 Cla

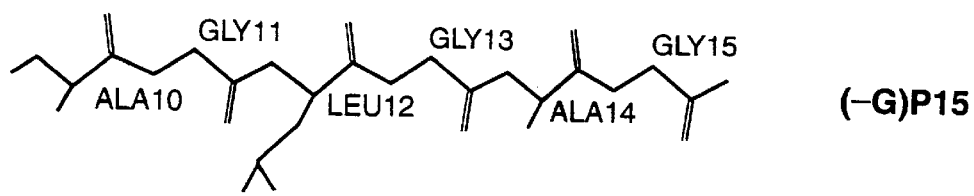
Fig. 1
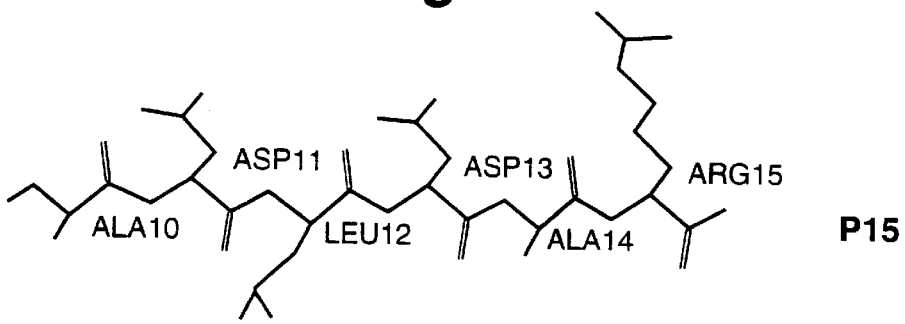
Fig. 2
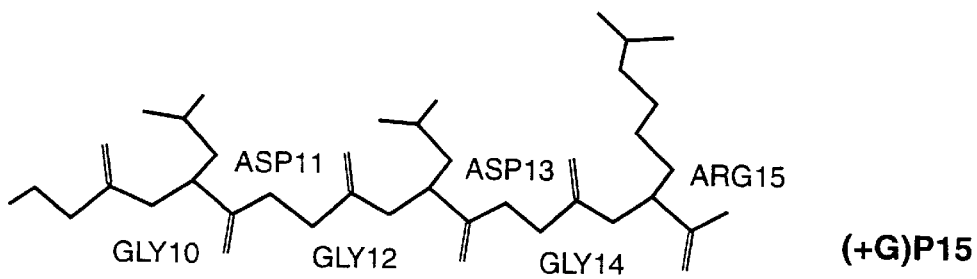
Fig. 3
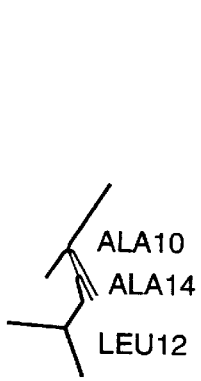 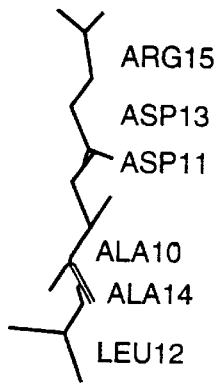 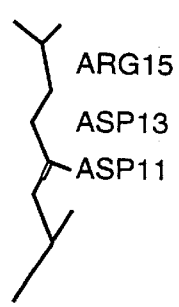
Fig. 4     Fig. 5     Fig. 6

ANTIGENIC PEPTIDES

This is a Continuation of application Ser. No. 08/763,302, filed Dec. 10, 1996, now U.S. Pat. No. 5,932,692.

This application is based on application No. MI95 A 002582 filed in Italy, the content of which is incorporated hereinto by reference.

This invention relates to improved antigenic peptides, methods for the preparation thereof, and use thereof.

It is known that antibodies recognise proteins important in diagnostic via binding to specific protein epitopes, formed generally by sequences 5 to 20 amino acids long.

In many cases, synthetic peptides corresponding to protein epitopes have been used for the preparation of diagnostic kits useful for the identification and/or the quantitative determination of antibodies associated to several pathologies. Identification of protein epitopes relevant for diagnostic use is carried out by producing, via chemical synthesis, peptides corresponding to different portions of the protein under examination, and evaluating the antigenic behavior thereof by means of a panel of sera of other biological fluids containing the corresponding antibody.

Very often, protein epitope structure is complex and their synthesis expensive.

Furthermore, chemical modification in the peptides identified as epitopes may lead, in an unpredictable way, to variations of the capability of antibody recognition (antigenicity), methadologies of broad applicability for improving, by making it more simple, the chemical structure of an antigenic peptide without altering the antigenic properties thereof are not yet available.

Therefore, there is still a great demand of an improvement in the structure of an antigenic peptide allowing manufacturing it at a lower cost, increasing the stability thereof against proteases, increasing the chemical stability thereof, and/or reducing aspecific interactions with other antibodies (antigenic cross-reactivity), without altering antigenic properties thereof.

Obviously, these advantages would have repercussions on the production of diagnostic kits, the use of said antigenic peptides as specific ligands for the purification of antibodies for diagnostic or therapy applications, and on the production of synthetic vaccines.

Surprisingly, it has now been found that these goals are reached when substituting one or more amino acids in the antigenic peptide sequence odd position, or respectively even, position with a glycine residue.

It is therefore a first object of this invention to provide an improved antigenic peptide, characterized in that the amino acid sequence, both normal and retro, is modified by replacing one or more amino acids with glycine, and that, when more than one amino acid is replaced, all the replaced amino acids are in odd position, or respectively, in even position, the amino acids having L or D configuration.

It is therefore a second object of this invention to provide a method for improving an antigenic peptide having a known amino sequence, characterized in that at least one amino acid in the sequence is replaced with glycine and that, when more than one amino acid is replaced, all the amino acids are replaced in the sequence even position, or respectively in the sequence odd position, and in that improved antigenic peptide, the amino acids having L or D configuration.

For sake of clarity, an antigenic peptide whose sequence is known and wherein, in the normal or retro sequence, at least one amino acid is replaced with glycine, will be hereinafter mentioned as "parent antigenic peptide".

Many are the "parent antigenic peptides" used in diagnostics for the preparation of kits employed for the determination of specific antibodies in serum and/or other biological fluids. For example, for HIV 1 or 2 infection diagnosis, peptides corresponding to the 586–610 env region of HIV virus are used, while for hepatitis C (HCV) infection in diagnostic kits are used peptides corresponding to regions E1, NS4, and NS5. A list of Chemical Abstract Registry Numbers to antigenic peptides (i.e. "parent antigenic peptides") which may be improved according to this invention is shown in the enclosed Table.

It is a third object of this invention to provide a diagnostic kit, characterized in that it contains at least one improved antigenic peptide as defined above.

It is a fourth object of this invention to provide the production of mono- or polyclonal antibodies able to recognize a respective "parent antigenic peptide", characterized in that a suitable animal is immunized with a corresponding improved antigenic peptide of this invention, blood or other suitable tissues are taken after a suitable time and the desired antibody is isolated according to conventional techniques, such as chromatography and precipitation. As it is known to the persons skilled in the art, blood is taken for the preparation of polyclonal antibodies, while other tissues, such as the spleen, are taken for the preparation of polyclonal antibodies.

It is a fifth object of this invention to provide a vaccine, characterized in that it comprises at least one improved antigenic peptide as defined above.

It is a sixth object of this invention to provide a method for antibody purification according to the ligands technique, characterized in that the ligand is an improved antigenic peptide as defined above.

The selection of the aminoacids to be replaced in odd or in even position in the antigenic peptide sequence should be driven by criteria well known to the persons skilled in the art, such as the cost, the coupling yield with the preceding and following amino acids, the complexity of protection and deprotection of the reactive groups, the chemical and enzymatic stability, and the like.

A typical example of amino acids which may be preferably substituted with glycine comprise: cysteine, arginine, asparagine, aspartic acid, glutamic acid, glutamine, histidine, lysine, serine, tyrosine, threonine, and tryptophan.

The improved antigenic peptides according to this invention may be easily prepared according to conventional techniques of the peptide chemistry which comprise suitable protection of amino acids, coupling of protected amino acids and removal of protecting groups.

Preferably, they are prepared according to the solid phase synthesis technique, which comprises the following steps:

coupling, using suitable reactants, of the first amino acid from the C-terminus protected by suitable groups both in the amino group and, when required, in the side chain, on a suitable support for solid phase synthesis, removal of the protecting groups at the amino group with suitable reactants, coupling of the following amino acid from the C-terminus, protected at the amino group and, when required, in the side chain, removal of the protecting group at the amino group and repetition of the coupling and deprotection cycles until all the amino acids comprised in the peptide sequence have been assembled, removal of all remaining side chain protecting groups from the assembled antigenic peptide and cleavage from the resin.

These techniques are widely described in the literature and well known to the persons skilled in the art. See, for example, Atherton & Sheppard, 1989, Solid Phase Peptide Synthesis: A practical approach, IRL Press, Oxford, UK.

Generally, the diagnostic use of the compounds of this invention in procedures for antibody determination comprises the formation of complexes with antibodies raised against the "parent antigenic peptide".

Typically, this technique comprises:
1) immobilizing at least one improved antigenic peptide of this invention on plastic ELISA microtiter plates, or on particles useful for diagnostic applications, either as they are or in form of conjugates with other molecules;
2) incubating a sample containing the desired antibody with the immobilized improved antigenic peptide;
3) washing the complex immobilized improved antigenic peptide/antibody; and
4) detecting the adsorbed antibody by means of a suitable reactant.

These techniques are widely described in the literature and are well known to the persons skilled in the art. See for example "Immunochemistry in Practice", Johnstone & Thorpe, (1987) Blackwell, Oxford, UK.

Preferably, step 1 is carried out using plastic microtiter plates, such as, for example, in PVC, with 96 wells filled with 0.1 M sodium bicarbonate solutions, pH 9.0, containing variable amounts (from 0 to 50 micrograms) of an improved antigenic peptide of this invention, previously conjugated to bovine serum albumin. After 24 hours incubation, the solution is removed, the microtiter plates are washed with phosphate buffer (pH 7.3), and the wells are filled with a 3% bovine albumin solution to eliminate sites of aspecific interaction.

In step 2, the microtiter plates are washed with phosphate buffer (pH 7.3), and the wells are filled with biological samples containing the antibodies to be determined. The plates are then incubated at 20–37° C. for 4–18 h.

Washing (step 3) is preferably carried out with phosphate buffer (pH 7.3).

Finally, step 4 is carried out by adding a solution containing an antibody anti-antibody to be determined (e.g. a rabbit antibody against human immunoglobulins) conjugated to the enzyme peroxidase. After 2 h incubation, the microtiter plates are washed again with phosphate buffer (pH 7.3). A solution of o-phenylenediamine is then added and color formation is detected using suitable plate readers.

Typically, the preparation of an antibody against an improved antigenic peptide able to recognize the corresponding "parent antigenic peptide" comprises:
1) immunizing a suitable animal, such as rabbit, sheep, rat, mouse or the like, with at least a suitable improved antigenic peptide according to this invention, possibly conjugated to a carrier proteins such as, for example, albumin and emocianyn, using suitable adjuvants;
2) blood sampling from said animal after a preselected period of time and separation of the serum fraction;
3) purifying the antibody according to conventional techniques such as, for example, chromatography or precipitation.

Also these techniques are well described in the literature and well known to the persons skilled in the art.

Typically the purification of an antibody against an antigenic peptide comprises the following steps:
1) immobilizing an improved antigenic peptide on a suitable support for affinity chromatography;
2) packing said support in a suitable chromatographic column;
3) equilibrating said column with a buffer favoring the interaction between the immunoglobulin and the antigen;
4) column loading with a fluid containing at least one immunoglobulin able to recognize the "parent antigenic peptide";
5) column washing with at least one buffer able to elute the impurities without affecting the interaction between immunoglobulin/improved antigenic peptide; and
6) elution of the previously adsorbed immunoglobulin from the column using a suitable dissociating eluent.

Steps 1) to 6) are carried out according to conventional techniques well known to the persons skilled in the art.

These and other features of this invention will become more evident from the following examples and from the enclosed figures where:

BRIEF DESCRIPTION OF THE DRAWINGS

FIG. 1 shows the planar view of the structure of an improved antigenic peptide of this invention of formula $NH_2$-Ala-Gly-Leu-Gly-Ala-Gly-COOH (referred to as (–G)P15) (SEQ ID NO:1); corresponding to the parent peptide P15 where all the amino acids in the even position are replaced with glycine.

FIG. 2 shows the planar view of the structure of the "parent antigenic peptide" P15 of formula $NH_2$-Ala-Asp-Leu-Asp-Ala-Arg-COOH. (SEQ ID NO:2); and FIG. 3 shows the planar view of the structure of the improved antigenic peptide of this invention of formula $NH_2$-Gly-Asp-Gly-Asp-Gly-Arg-COOH (SEQ ID NO:3) (referred to as (+G)P15) corresponding to the "parent antigenic peptide" P15 where all the aminoacids in the odd position are replaced with glycine.

FIG. 4 is the axial view of the peptide of FIG. 1.

FIG. 5 is the axial view of the peptide of FIG. 2.

FIG. 6 is the axial view of the peptide of FIG. 3.

FIGS. 1–6 show that the improved antigenic peptide (–G)P1 5 maintains all the side chains located below the peptide backbone of the "parent antigenic peptide". The improved antigenic peptide (+G)P15 maintains all the side chains in the upper part of the parent antigenic P15.

EXAMPLE 1

Figure 7:
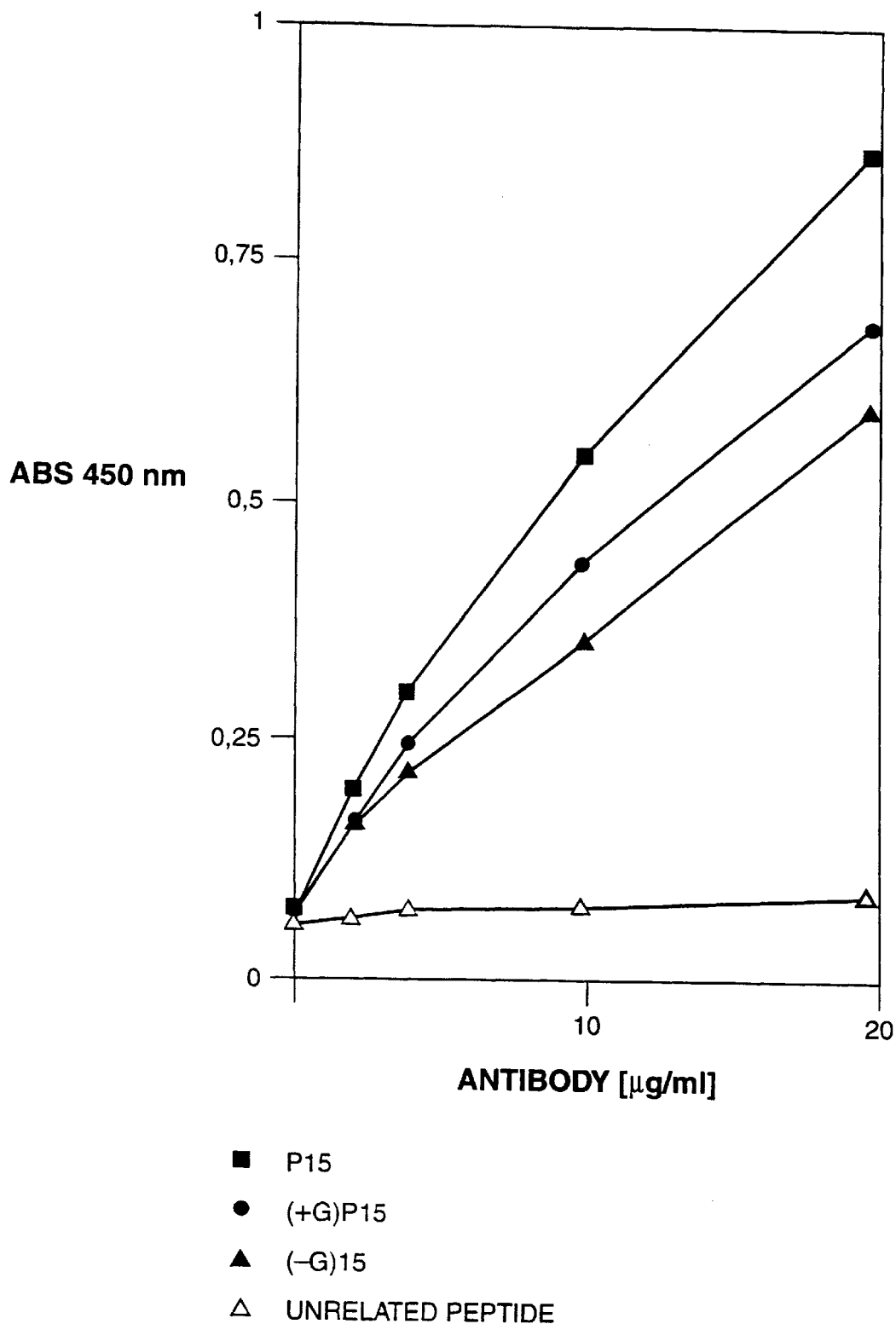
FIG. 7 shows the interaction between antibodies raised against the "parent antigenic peptide" P15 and peptide P15, improved antigenic peptides of this invention (–G)P15 and (+G)P15, and an unrelated peptide.

Preparation of Improved Antigenic Peptides and Determination of Their Antigenic Properties Polyclonal antibodies have been prepared by rabbit immunization with the "parent antigenic peptide" P15 ($NH_2$-Ala-Asp-Leu-Asp-Ala-Arg-COOH) conjugated to bovine serum albumin.

The corresponding improved antigenic peptides have also been prepared.

A first improved antigenic peptide has been obtained replacing the residues in even position with glycine. The corresponding peptide having the sequence $NH_2$-Ala-Gly-Leu-Gly-Ala-Gly-COOH has thus been obtained, which is hereinafter referred to as (–G)P15.

A second improved antigenic peptide has been obtained via replacement of the residues in the odd position with glycine. The corresponding peptide having sequence NH$_2$-Gly-Asp-Gly-Asp-Gly-Arg-COOH has been thus obtained, which is hereinafter referred to as (+G)P15.

Compounds P15, (+G)P15, and (−G)P15 have been synthesized with an automatic peptide synthesizer (ABI 431-A, software version 1.1, Perkin-Elmer, U.S.A.) following the protocols suggested by the manufacturer and based on methodologies described in the literature (Atherton & Sheppard, 1989, Solid Phase Peptide Synthesis: A practical approach, IRL Press, Oxford, UK).

The synthesis has been carried out starting from a acid-labile resin for peptide synthesis prederivatized with glycine (Novabiochem Cat. No. 04-12-2800, 0.1 mmole) for (−G)P15 peptide and from arginine (Novabiochem Cat. No. 04-12-2850, 0.1 mmol) for antigenic peptides P15 and (+G)P15. Both glycine and arginine were protected at the N-terminal amino group a Fmoc group which, in the first synthesis cycle, has been removed by treatment with 3.0 ml of piperidine (20% in N-methyl-pyrrolidone)(ABI Cat No. 400629) for 14 minutes at room temperature under stirring.

The deprotected resin has been then washed 5 times with 2.5 ml of N-methyl-2-pyrrolidone (Merck Cat. No. 806072) for 9 minutes under shaking at room temperature.

In the meantime the amino acid residue in position 2 from the C-terminus (1 mmole) has been preactivated by incubation with 1 ml of HOBt 1 M dissolved in N-methyl-2-pyrrolidone (ABI Cat. No. 400662) and 1 ml of 1 M dicyclohexylcarbodiimide in N-methyl-2-pyrrolidone (ABI Cat. No. 400663).

The activated amino acid has been then incubated with the resin for 51 minutes under constant shaking. After washing with N-methyl-2-pyrrolidone (4 washes for 0.5 minutes with 2 ml) the resin underwent a further deprotection cycle with piperidine and a further coupling cycle with the next amino acid. This sequential steps procedure has been repeated until all the amino acid residues have been assembled. In detail, the following amino acid derivatives have been used: Fmoc-Asp(tBu) (Novabiochem Cat. No. 04-12-1013), Fmoc-Ala (Novabiochem Cat. No. 04-12-1006); Fmoc-Leu (Novabiochem Cat. No. 04-12-1025. After completion of synthesis cycles, and removal of the N-terminal Fmoc group by piperidine treatment, the resin has been washed with methanol, dichloromethane, and again with methanol and carefully dried under vacuum for 12 h. Afterwards, the peptide has been detached from the resin by incubation of 100 mg of resin with 5 ml of a mixture of trifluoroacetic acid (Pierce Cat. No.28901)/phenol (Carlo Erba Cat. No. 451285)/water (Merck Cat. No.15333) ethanedithiol (Aldrich Cat No. E 360-0)/thioanisol (Aldrich Cat. No. T 2,800-2) 84:4:3:3:3 v/v for 2 h at room temperature under shaking. The resin has been then filtered using a sintered glass filter. The filtrate has been reduced in volume to few ml by vacuum evaporation and the residual liquid has been treated with 50 ml of cold ethyl ether. The precipitated peptidic material has been then separated by centrifugation and the centrifuged material resuspended in 25 ml of water/acetonitrile/TFA 50:50:0.1, frozen and lyophilized. At the end, the lyophilized material has been purified from contaminants by high performance liquid chromatography (HPLC) using a Lichrospher RP-8 column (25×1 cm I.D.) (Merck Cat. No. 150153), equilibrated at a flow rate of 3 ml/min with water/acetonitrile/TFA 95/5/0.1, and eluting with a linear gradient of acetonitrile ranging from 5% to 80% in 55 minutes. Material corresponding to the main peak has been collected, frozen, and lyophilized.

The antigenic peptides thus obtained have been conjugated to bovine serum albumin using glutaraldheyde according to known procedures (Immunochemistry in Practice, Johnstone & Thorpe, (1987) Blackwell, Oxford, UK), dialyzed against 0.1 M acetic acid, and lyophilized.

Microtiter plates for ELISA determination (Falcon Cat. No. 3912) have been treated with the peptides conjugated to BSA in concentration of from 0 to 50 µg/ml in a sodium bicarbonate buffer pH 9.0, for 12 h at 4° C. The plates have been washed with a 150 mM sodium phosphate buffer, pH 7.2 (PBS) and then, to each well of the plate, 200 microliters of a PBS solution containing 3% bovine serum albumin (BSA, Sigma Cat. NO. A-4503) have been added.

After one hour, the plates have been washed again 4 times with PBS, and each well has been filled with solutions (100 µl) containing rabbit antibodies against peptide P15, in concentration of from 0 to 20 µg/ml. After 2 hours incubation, plates have been washed 8 times with PBS and then in each well 100 µl of a solution containing anti-rabbit immunoglobulin goat immunoglobulins conjugated to peroxidase (Sigma Cat. No. A-6154) diluted 1:100 with PBS containing 3% BSA have been added. After one hour, the plates have been washed again with PBS. Then each well has been filled with 100 µl of a solution containing 1 mg/ml of o-phenylenediamine (Sigma P 6912) in 0.1 M sodium citrate, and 5 mM hydrogen peroxide. After 30 minutes, the reaction has been stopped by adding 25 microliters of 4.5 M sulfuric acid. The absorbance at 490 nm of each well has been determined using a plate reader (Merck, Mod. MIOS). The results are shown in FIG. 7.

The specificity of the interactions observed has been determined by inhibition studies, via incubation of the antibody directed against peptide P15 with peptides P15, (−G)P15, (+G)P15 at varying concentrations.

Figure 8:
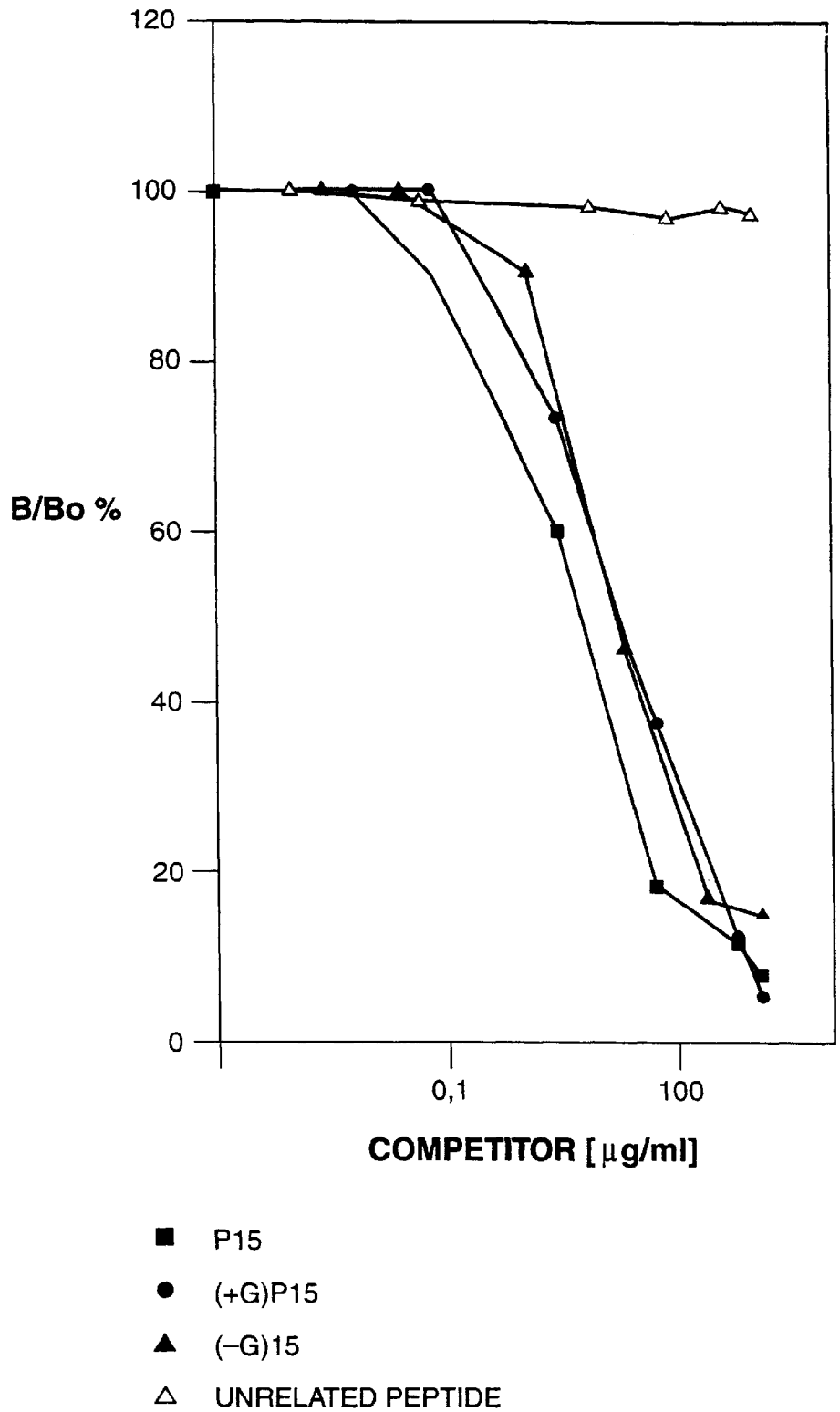
FIG. 8 shows that the interaction between antibodies raised against the "parent antigenic peptide" P15 and peptide P15 is inhibited in the presence of improved antigenic peptides (–G)P14 and (+G)P15 and peptide P15 itself, but not in the presence of unrelated peptides.

As shown in FIG. 7, immunoglobulins became associated to the antigenic peptides P15, (−G)P15, and (+G)P15, immobilized on the plate, in a dose dependent fashion and with about the same intensity. The interaction is inhibited in the presence of peptides P15, (−G)P15, and (+G)P15 in solution in a dose dependent manner and specifically while control peptides (BSA, or an unrelated peptide) do not inhibit the interaction (FIG. 8).

Similar recognition properties have been shown by improved antigenic peptides of this invention (−G)P15 and (+G)P15 when produced from amino acids having all D configuration, and by improved antigenic peptides of this invention having reversed sequence direction. Indeed, peptides NH$_2$-Gly-Ala-Gly-Leu-Gly-Ala-COOH, corresponding to peptide (−G)P15 with reversed sequence, and NH$_2$-Arg-Gly-Asp-Gly-Asp-Gly-COOH, corresponding to peptide (+G)P15 with reversed sequence, both in configuration all L or all D, showed similar functional properties.

EXAMPLE 2

Purification of Anti-P15 Antibodies on Columns Prepared By Immobilizing (−G)P15 and (+G)P15

The improved antigenic peptides (−G)P15 and (+G)P15 (5 mg) of this invention have been dissolved separately in 5 ml of a 0.1 M sodium bicarbonate buffer, pH 9.0, and then added to 1.2 g of Eupergit C30 N resin (Sigma Cat. No. 0 9879), affinity chromatography support preactivated with epoxyde groups for the direct coupling of peptides and proteins, respectively. The suspension has been shaken for 24 h and the coupling extent has been monitored by sampling of the reaction mixture followed by RP-HPLC analysis. In both cases, about 85% of initial peptide was covalently coupled to the support after 24 h.

The derivatized resins have then been washed with 50 ml of 1 M Tris pH 9.0, and packed on glass columns 100×6.6 mm I.D. For purification procedures, the columns have been equilibrated with Tris buffer 50 mM, pH 7.0, at a flow rate of 1 ml/min. while monitoring the effluent at 280 nm. On the two columns, 1 ml of crude rabbit serum, containing antibodies against peptide P15, has been applied and, after elution of non retained material at the column void volume, the eluent has been changed to 0.1 M acetic acid.

Material desorbed by such treatment has been collected and analyzed by electrophoretic analysis on polyacrylamide gels. In both cases, the columns have been able to purify efficiently the anti-P15 antibodies in the serum. Similar recognition properties have been showed by the improved antigenic peptides of this invention (−G)P15 and (+G)P15 produced from amino acids having D configuration, as well as by improved antigenic peptides of this invention having reversed sequence. Indeed, both peptides $NH_2$-Gly-Ala-Gly-Leu-Gly-Ala-COOH, corresponding to peptide (−G)P15 with reversed sequence, and $NH_2$-Arg-Gly-Asp-Gly-Asp-Gly-COOH, corresponding to peptide (+G)P15 with reversed sequence, showed similar functional properties, both in configuration all L or all D.

EXAMPLE 3

Production of Antibodies Against (−G)P15 and (+G)P15 in Rabbits

Improved antigenic peptides of this invention (−G)P15 and (+G)P15 conjugated to BSA, prepared as previously described, have been used for rabbits (New Zealand) immunization by injections in the rear foot pads. After 4 weeks, a subsequent boost with the same improved antigenic peptides has been carried on, and after 2 months blood samples have been taken for the preparation of the serum fraction.

As detected using ELISA technique as described above and using microtiter plates for ELISA determinations sensitized with peptide P15, sera obtained from the two different immunizations were able to recognize peptide P15 showing an affinity and selectivity degree comparable to those shown by the antiserum against parent peptide P15.

Similar recognition properties have been shown by improved antigenic peptides of this invention (−G)P15 and (+G)P15 produced from amino acids having D configuration, as well as by improved antigenic peptides of this invention having reversed sequence.

Indeed, both peptides $NH_2$-Gly-Ala-Gly-Leu-Gly-Ala-COOH, corresponding to peptide (−G)P15 with reversed sequence, and $NH_2$-Arg-Gly-Asp-Gly-Asp-Gly-COOH, corresponding to peptide (+G)P15 with reversed sequence, both in configuration all L or all D, showed similar functional properties.

TABLE

| | | | | | | |
|---|---|---|---|---|---|---|
| 121478-87-3 | 131143-43-6 | 119330-55-1 | 119330-56-2 | 119330-57-3 | 131143-38-9 | 134908-81-9 |
| 134908-82-0 | 134908-79-5 | 134908-80-8 | 129403-71-0 | 133334-08-4 | 132965-90-3 | 115283-36-8 |
| 117628-43-0 | 118389-56-3 | 119699-13-7 | 119699-12-6 | 119699-14-8 | 119699-15-9 | 119699-16-0 |
| 119699-17-1 | 126729-43-9 | 131200-77-6 | 131093-03-3 | 131280-39-2 | 126546-16-5 | 126546-17-6 |
| 126546-19-8 | 126546-14-3 | 126546-15-4 | 126546-18-7 | 134547-78-7 | 121272-75-1 | 121272-70-6 |
| 128513-74-6 | 128513-76-8 | 128513-75-7 | 128513-52-0 | 128513-80-4 | 128513-77-9 | 128513-78-0 |
| 127496-43-9 | 128027-09-8 | 127496-49-5 | 127496-48-4 | 127496-47-3 | 124148-04-5 | 128027-04-3 |
| 127496-50-8 | 129710-61-8 | 129710-60-7 | 129710-63-0 | 134945-29-2 | 132866-87-6 | 130037-19-3 |
| 130037-20-6 | 103351-42-4 | 134145-91-8 | 118113-84-1 | 119440-22-1 | 114680-04-5 | 123608-06-0 |
| 123608-07-1 | 121683-16-7 | 121683-17-8 | 123608-08-2 | 123608-09-3 | 124024-82-4 | 124024-83-5 |
| 124024-84-6 | 124024-85-7 | 94361-68-9 | 86025-40-3 | 107720-45-6 | 107720-46-7 | 117276-07-0 |
| 86025-41-4 | 117536-69-3 | 87608-92-2 | 99731-72-3 | 121683-18-9 | 121683-19-0 | 123608-10-6 |
| 114355-74-7 | 114355-75-8 | 114355-76-9 | 114355-77-0 | 114355-78-1 | 114355-79-2 | 114355-80-5 |
| 114355-81-6 | 114355-82-7 | 112195-83-2 | 118103-21-2 | 118103-22-3 | 118103-23-4 | 118103-24-5 |
| 106440-45-3 | 106440-43-1 | 106440-44-2 | 123056-69-9 | 123608-11-7 | 123608-12-8 | 137544-82-2 |
| 129773-36-0 | 129403-69-6 | 129403-68-5 | 129403-77-6 | 134145-93-0 | 134145-94-1 | 134145-92-9 |
| 134145-95-2 | 134145-96-3 | 134145-97-4 | 134145-98-5 | 134146-64-8 | 134145-99-6 | 134146-00-2 |
| 134146-01-3 | 134146-02-4 | 134146-63-7 | 134146-62-6 | 134146-65-9 | 129403-76-5 | 132654-55-8 |
| 121256-87-9 | 136627-97-9 | 133134-51-7 | 133134-50-6 | 121478-86-2 | 108421-86-9 | 119330-53-9 |
| 119330-54-0 | 119330-52-8 | 136799-67-2 | 123938-62-5 | 110157-83-0 | 126729-44-0 | 121546-71-2 |
| 133134-53-9 | 133134-54-0 | 133134-52-8 | 133134-56-2 | 133134-55-1 | 118113-88-5 | 118113-89-6 |
| 124542-66-1 | 133134-57-3 | 137085-93-9 | 137085-94-0 | 136361-96-1 | 130730-37-9 | 130730-38-0 |
| 130730-35-7 | 130730-36-8 | 131333-19-2 | 116783-38-1 | 126729-45-1 | 132989-34-5 | 132989-35-6 |
| 134547-80-1 | 134547-81-2 | 130527-74-1 | 134773-23-2 | 134146-03-5 | 134773-24-3 | 133107-89-8 |
| 122096-66-6 | 122096-67-7 | 127712-26-9 | 105080-81-7 | 134773-25-4 | 134773-26-5 | 126902-84-9 |
| 126902-85-0 | 128794-23-0 | 126467-93-4 | 108778-09-2 | 118901-31-8 | 123626-27-7 | 118901-30-7 |
| 125006-38-4 | 128511-32-0 | 128511-28-4 | 128511-29-5 | 128511-31-9 | 128511-30-8 | 130809-05-1 |
| 130809-06-2 | 130809-07-3 | 130809-08-4 | 129804-69-9 | 129804-68-8 | 129804-71-3 | 129804-70-2 |
| 130809-09-5 | 130809-10-8 | 130809-11-9 | 125807-38-7 | 125807-37-6 | 134773-28-7 | 128393-14-6 |
| 128393-15-7 | 136251-99-5 | 115250-87-8 | 115250-85-6 | 126039-23-4 | 134012-76-3 | 130843-53-7 |
| 125052-49-5 | 125052-51-9 | 125913-27-1 | 125052-54-2 | 125052-55-3 | 125052-56-4 | 125052-57-5 |
| 125052-58-6 | 125913-25-9 | 125912-55-2 | 125913-05-5 | 125913-26-0 | 125934-29-4 | 125934-75-0 |
| 125913-28-2 | 128122-97-4 | 125912-48-3 | 125912-61-0 | 125934-21-6 | 125912-57-4 | 125934-25-0 |
| 125913-24-8 | 118842-09-4 | 118842-10-7 | 121272-71-7 | 124670-01-5 | 136894-52-5 | 128907-18-6 |
| 128907-19-7 | 128907-20-0 | 128907-21-1 | 129069-07-4 | 129069-08-5 | 129069-09-6 | 128393-16-8 |
| 126467-94-5 | 126467-95-6 | 131198-28-2 | 110908-53-7 | 110908-54-8 | 126467-96-7 | 126467-97-8 |
| 131015-34-4 | 131015-35-5 | 126467-98-9 | 126467-99-0 | 128002-44-8 | 128002-42-6 | 128002-45-9 |
| 128002-41-5 | 128002-43-7 | 123896-18-4 | 123896-19-5 | 136108-04-8 | 108528-73-0 | 119166-46-0 |
| 108528-72-9 | 119166-45-9 | 127651-24-5 | 135114-31-7 | 135114-32-8 | 127004-06-2 | 127004-07-3 |
| 129875-14-5 | 129070-22-0 | 137467-86-8 | 137467-87-9 | 137467-76-6 | 126729-46-2 | 128123-00-2 |
| 128122-99-6 | 128122-98-5 | 131595-96-5 | 131595-97-6 | 125385-26-4 | 125385-27-5 | 122071-94-7 |
| 123757-99-3 | 118689-46-6 | 133423-86-6 | 137544-80-0 | 126468-00-6 | 132188-68-2 | 80043-31-8 |
| 134908-83-1 | 134908-84-2 | 119939-22-9 | 119939-23-0 | 128280-57-9 | 135114-30-6 | 128280-58-0 |

TABLE-continued

| | | | | | | |
|---|---|---|---|---|---|---|
| 134146-58-0 | 130453-66-6 | 112487-44-2 | 106120-44-9 | 114822-09-2 | 132965-92-5 | 132965-93-6 |
| 136894-53-6 | 136894-54-7 | 95725-97-6 | 135230-90-9 | 118113-81-8 | 125934-27-2 | 115469-09-5 |
| 122635-71-6 | 136697-92-2 | 118113-87-4 | 129875-15-6 | 137011-45-1 | 129875-16-7 | 125052-50-8 |
| 135314-79-3 | 123757-98-2 | 118113-86-3 | 118113-85-2 | 128511-33-1 | 119166-44-8 | 134773-27-6 |
| 125934-22-7 | 125052-52-0 | 125052-53-1 | 113914-09-3 | 123139-70-8 | 122633-78-7 | 126601-42-1 |
| 124204-12-2 | 128513-79-1 | 134908-86-4 | 134908-85-3 | 125521-89-3 | 125521-90-6 | 127186-56-5 |
| 115088-64-7 | 115088-65-8 | 115088-63-6 | 115088-57-8 | 116977-51-6 | 105635-53-8 |  |
| 104981-28-4 | 124759-02-0 | 124759-03-1 | 106640-40-8 | 127609-27-2 | 127609-28-3 | 127186-55-4 |
| 133134-44-8 | 125858-11-9 | 133134-45-9 | 133134-47-1 | 133134-46-0 | 129652-43-3 | 127067-92-9 |
| 127067-93-0 | 132729-32-9 | 132729-16-9 | 134033-70-8 | 119699-08-0 | 119699-09-1 | 119699-10-4 |
| 119699-11-5 | 124543-12-0 | 124543-14-2 | 124543-16-4 | 124543-18-6 | 124543-13-1 | 124543-15-3 |
| 124543-17-5 | 124543-19-7 | 130703-40-1 | 130703-41-2 | 130703-42-3 | 130703-43-4 | 113535-61-8 |
| 113535-62-9 | 118440-37-2 | 118440-39-4 | 118440-38-3 | 118440-40-7 | 131093-02-2 | 128605-22-1 |
| 118440-41-8 | 118440-42-9 | 136394-39-3 | 136394-36-0 | 124892-13-3 | 106440-41-9 | 106440-42-0 |
| 116242-95-6 | 116267-41-5 | 110734-87-7 | 110734-88-8 | 112385-90-7 | 112385-91-8 | 115515-39-4 |
| 115515-40-7 | 134088-68-9 | 134088-69-0 | 121549-68-6 | 122318-62-1 | 122318-63-2 | 128794-19-4 |
| 128794-20-7 | 121546-69-8 | 121546-70-1 | 131200-78-7 | 131015-32-2 | 131015-33-3 | 129202-45-5 |
| 98845-93-3 | 125004-36-6 | 127497-68-1 | 98845-94-4 | 124541-45-3 | 123840-84-6 | 134496-56-3 |
| 129202-46-6 | 107898-19-1 | 107898-20-4 | 113065-69-3 | 134496-60-9 | 108727-19-1 | 108727-20-4 |
| 132049-93-5 | 113014-94-1 | 113014-95-2 | 121684-98-8 | 121684-96-6 | 121684-99-9 | 121684-97-7 |
| 121685-00-5 | 127496-45-1 | 127496-46-2 | 125121-95-1 | 125121-96-2 | 96024-40-7 | 96024-41-8 |
| 122390-61-8 | 122390-62-9 | 134373-30-1 | 134373-31-2 | 136331-36-7 | 136331-37-8 | 117680-75-8 |
| 117680-76-9 | 122633-76-5 | 122633-77-6 | 125854-13-9 | 125854-14-0 | 123608-04-8 | 123608-05-9 |
| 126468-01-7 | 126468-02-8 | 120797-41-3 | 120797-42-4 | 114964-74-8 | 116410-74-3 | 116410-75-4 |
| 135494-31-4 | 129069-05-2 | 129069-06-3 | 130300-79-7 | 130300-82-2 | 130300-77-5 | 130300-80-0 |
| 130300-78-6 | 130300-81-1 | 133483-02-0 | 133483-03-1 | 128794-17-2 | 128794-18-3 | 113913-65-8 |
| 113913-67-0 | 129130-32-1 | 129130-33-2 | 121256-85-7 | 121256-86-8 | 128513-72-4 | 121127-21-7 |
| 129652-44-4 | 129652-45-5 | 123081-69-6 | 129130-31-0 | 135433-10-2 | 125854-15-1 | 127384-61-6 |
| 136894-51-4 | 136628-04-1 | 136628-05-2 | 134710-70-6 | 133925-44-7 | 126546-13-2 | 126546-12-1 |
| 121853-65-4 | 134375-81-8 | 137261-57-5 | 123840-86-8 | 123840-87-9 | 116676-70-1 | 123840-88-0 |
| 126966-92-5 | 123840-89-1 | 123840-90-4 | 123840-91-5 | 134496-57-4 | 134496-61-0 | 127497-64-7 |
| 123840-92-6 | 123840-93-7 | 123840-94-8 | 126966-90-3 | 123840-95-9 | 123840-96-0 | 123840-97-1 |
| 123840-98-2 | 127497-65-8 | 133533-77-4 | 118605-80-4 | 135541-91-2 | 135541-92-3 | 123840-99-3 |
| 123841-00-9 | 132965-91-4 | 124362-97-6 | 123841-01-0 | 123841-02-1 | 123841-03-2 | 126966-91-4 |
| 123841-04-3 | 123841-05-4 | 124362-98-7 | 134033-71-9 | 134033-72-0 | 123841-06-5 | 123841-07-6 |
| 128963-22-4 | 124362-99-8 | 124363-00-4 | 124363-01-5 | 124363-02-6 | 124363-03-7 | 124363-04-8 |
| 124363-05-9 | 124363-06-0 | 124363-07-1 | 124363-08-2 | 124363-09-3 | 124363-10-6 | 124363-11-7 |
| 124363-12-8 | 124363-13-9 | 124363-14-0 | 124363-15-1 | 124363-16-2 | 123841-08-7 | 123841-09-8 |
| 134496-59-6 | 134496-63-2 | 135526-94-2 | 123841-10-1 | 123841-11-2 | 124669-99-4 | 123841-12-3 |
| 127497-66-9 | 127497-67-0 | 127497-69-2 | 116676-71-2 | 134496-58-5 | 134496-62-1 | 123840-85-7 |
| 124670-00-4 | 133722-28-8 | 133722-30-2 | 133722-31-3 | 133722-33-5 | 133722-32-4 | 133722-35-7 |
| 133722-34-6 | 133722-36-8 | 133722-39-1 | 133722-40-4 | 133722-41-5 | 133722-42-6 | 121852-69-5 |
| 137261-26-8 | 121852-69-5 | 137261-26-8 | 137261-33-7 | 137261-21-3 | 137261-31-5 | 137261-35-9 |
| 137261-24-6 | 137261-38-2 | 137261-11-1 | 137261-16-6 | 137261-25-7 | 137261-28-0 | 137261-34-8 |
| 137261-23-5 | 137261-37-1 | 128393-09-9 | 128393-10-2 | 128513-73-5 | 127547-56-2 | 121852-88-8 |
| 135526-21-5 | 116676-72-3 | 137094-71-4 | 137094-77-0 | 135433-07-7 | 135433-08-8 | 135433-09-9 |
| 126627-00-7 | 126627-01-8 | 114470-70-1 | 114470-71-2 | 125006-39-5 | 114470-72-3 | 114470-73-4 |
| 114470-74-5 | 114470-75-6 | 126627-02-9 | 126627-03-0 | 122525-01-3 | 122525-02-4 | 136331-35-6 |
| 128687-65-0 | 128687-66-1 | 128002-39-1 | 128002-36-8 | 128002-38-0 | 126902-80-5 | 126902-81-6 |
| 126902-79-2 | 126902-82-7 | 126902-78-1 | 126902-83-8 | 127495-76-5 | 127494-77-6 | 127495-78-7 |
| 127495-79-8 | 116676-85-8 | 131280-40-5 | 131280-41-6 | 128511-34-2 | 125723-33-3 | 125723-34-4 |
| 123081-70-9 | 123081-71-0 | 117276-08-1 | 117276-09-2 | 117276-15-0 | 117276-16-1 | 117276-11-6 |
| 117276-12-7 | 128393-11-3 | 128393-12-4 | 111906-01-5 | 108136-48-7 | 118901-27-2 | 118901-28-3 |
| 118901-29-4 | 125725-23-7 | 125725-24-8 | 125725-25-9 | 128392-86-9 | 117276-10-5 | 117276-17-2 |
| 117276-13-8 | 115630-29-0 | 115630-26-7 | 128392-63-2 | 117276-18-3 | 117276-14-9 | 128392-83-6 |
| 128392-62-1 | 115630-36-9 | 128393-13-5 | 128392-84-7 | 128392-64-3 | 125385-20-8 | 125385-21-9 |
| 124834-94-2 | 124834-95-3 | 131359-89-2 | 105932-76-1 | 126141-24-5 | 129875-13-4 | 130151-85-8 |
| 107564-98-7 | 111642-48-9 | 136217-34-0 | 136217-33-9 | 92480-13-2 | 125854-16-2 | 120112-33-6 |
| 110908-37-7 | 110908-38-8 | 108173-92-8 | 108173-93-9 | 133198-14-8 | 133198-15-9 | 115469-07-3 |
| 115469-08-4 | 118901-26-1 | 120858-93-7 | 118689-37-5 | 117924-89-7 | 122156-87-0 | 117924-88-6 |
| 125913-23-7 | 128768-80-9 | 135231-06-0 | 133557-22-9 | 133557-26-3 | 133557-25-2 | 133557-24-1 |
| 133557-23-0 | 136331-38-9 | 133758-63-1 | 133758-64-2 | 133134-48-2 | 133134-49-3 | 126466-51-1 |
| 126466-52-2 | 131595-94-3 | 131595-95-4 | 130958-64-4 | 117055-82-0 | 130958-65-5 | 130958-66-6 |
| 113608-98-3 | 127361-05-1 | 127361-06-2 | 133352-97-3 | 129978-66-1 | 129978-44-5 | 129978-62-7 |
| 130938-48-6 | 130938-50-0 | 130938-51-1 | 134496-64-3 | 134214-87-2 | 134214-88-3 | 126904-30-1 |
| 126904-29-8 | 130588-13-5 | 130588-14-6 | 111309-64-9 | 114921-08-3 | 112415-11-9 | 123081-72-1 |
| 124056-55-9 | 130002-75-4 | 130002-78-7 | 130002-76-5 | 130002-79-8 | 130002-77-6 | 130002-80-1 |
| 130002-81-2 | 130002-82-3 | 130002-83-4 | 125807-39-8 | 125807-40-1 | 126124-10-5 | 126124-12-7 |
| 126124-11-6 | 126124-13-8 | 119440-21-0 | 119631-31-1 | 129817-71-6 | 129817-72-7 | 122635-72-7 |
| 122635-73-8 | 128087-23-0 | 135494-12-1 | 135494-11-0 | 135494-19-8 | 124228-52-0 | 124228-53-1 |
| 113956-04-0 | 113956-05-1 | 133064-05-8 | 133064-06-9 | 117149-13-0 | 127186-50-9 | 127186-46-3 |
| 127186-51-0 | 127186-48-5 | 112264-04-7 | 112264-05-8 | 116410-76-5 | 116410-77-6 | 133652-22-9 |
| 128963-23-5 | 128963-24-6 | 137011-46-2 | 137011-47-3 | 126627-04-1 | 111069-30-8 | 114964-75-9 |
| 114964-76-0 | 133423-87-7 | 96351-91-6 | 105646-96-6 | 128415-67-8 | 128415-68-9 | 126546-20-1 |
| 126546-22-3 | 106440-46-4 | 123780-37-0 | 123780-38-1 | 126546-21-2 | 126546-23-4 | 126546-24-5 |
| 126546-25-6 | 101462-84-4 | 102037-21-8 | 126546-26-7 | 126546-27-8 | 125006-40-8 | 125006-41-9 |
| 123422-95-7 | 123422-96-8 | 124543-20-0 | 124543-21-1 | 116917-63-6 | 130037-21-7 | 130037-22-8 |
| 123422-97-9 | 123422-98-0 | 137011-48-4 | 134547-79-8 | 125006-42-0 | 125006-43-1 | 125723-31-1 |
| 125723-32-2 | 125385-22-0 | 125385-23-1 | 137011-49-5 | 125385-24-2 | 125385-23-5 | 137011-50-8 |

TABLE-continued

| | | | | | | |
|---|---|---|---|---|---|---|
| 124301-41-3 | 124301-42-4 | 110908-39-9 | 110908-40-2 | 110908-41-3 | 110908-42-4 | 125858-12-0 |
| 125858-13-1 | 125006-44-2 | 88652-32-8 | 89925-73-5 | 89925-72-4 | 122495-30-1 | 122495-33-4 |
| 122495-34-5 | 122495-26-5 | 122495-27-6 | 122495-28-7 | 122495-29-8 | 122495-31-2 | 122495-32-3 |
| 101962-78-1 | 126627-05-2 | 110908-43-5 | 110908-44-6 | 116133-97-2 | 116133-98-3 | 111516-71-3 |
| 111516-72-4 | 111516-73-5 | 111516-74-6 | 111516-67-7 | 111516-69-9 | 112844-54-9 | 112844-55-0 |
| 112844-56-1 | 111516-76-8 | 111516-78-0 | 111516-75-7 | 111516-77-9 | 122653-14-9 | 122653-15-0 |
| 110908-47-9 | 110908-45-7 | 110908-46-8 | 126627-06-3 | 126627-08-5 | 126627-07-4 | 126627-09-6 |
| 116242-96-7 | 116242-97-8 | 116242-98-9 | 111364-90-0 | 111364-91-1 | 129495-13-2 | 129495-14-3 |
| 126466-53-3 | 126466-54-4 | 126466-57-7 | 126194-37-4 | 126194-36-3 | 134033-73-1 | 134033-74-2 |
| 107460-02-6 | 92228-83-6 | 92228-85-8 | 86090-10-0 | 90371-79-2 | 110908-49-1 | 110908-50-4 |
| 134033-76-4 | 134033-77-5 | 134033-78-6 | 110908-51-5 | 110908-52-6 | 126466-55-5 | 126466-56-6 |
| 126466-59-9 | 112263-99-7 | 111365-96-9 | 111365-97-0 | 116242-99-0 | 111365-98-1 | 111365-99-2 |
| 111516-79-1 | 112264-00-3 | 105932-77-2 | 105932-78-3 | 112264701-4 | 112264-02-5 | 111518-10-6 |
| 111518-11-7 | 112264-03-6 | 126096-73-9 | 126096-74-0 | 128338-85-2 | 128338-86-3 | 125854-17-3 |
| 125854-18-4 | 119937-15-4 | 119937-16-5 | 124892-14-4 | 124892-15-5 | 111518-12-8 | 111518-13-9 |
| 125006-45-3 | 111516-80-4 | 111516-82-6 | 111516-81-5 | 111516-83-7 | 100178-18-5 | 120112-34-7 |
| 120112-35-8 | 117680-77-0 | 117680-78-1 | 126194-38-5 | 130237-53-5 | 127885-03-4 | 130237-58-0 |
| 130237-59-1 | 130237-60-4 | 130237-61-5 | 130237-62-6 | 130237-54-6 | 130237-63-7 | 130237-64-8 |
| 130237-55-7 | 130237-56-8 | 130237-57-9 | 128825-84-3 | 99549-13-0 | 99549-14-1 | 134033-75-3 |
| 133064-03-6 | 133064-04-7 | 130068-17-6 | 130068-18-7 | 111364-92-2 | 111364-93-3 | 122635-74-9 |
| 113441-47-7 | 84842-64-8 | 109456-76-0 | 109456-77-1 | 125699-16-3 | 129267-52-3 | 129267-53-4 |
| 125546-52-3 | 125546-53-4 | 125546-51-2 | 125546-54-5 | 125546-55-6 | 121226-71-9 | 121226-72-0 |
| 132188-67-1 | 122006-55-7 | 119937-17-6 | 127384-62-7 | 119937-18-7 | 127384-63-8 | 122006-56-8 |
| 127384-64-9 | 129288-94-4 | 128280-56-8 | 123448-77-1 | 123448-78-2 | 126966-94-7 | 123448-76-0 |
| 128002-40-4 | 123896-14-0 | 123896-15-1 | 126468-03-9 | 120366-09-8 | 123081-74-3 | 123081-73-2 |
| 125199-77-1 | 125199-78-2 | 135846-15-0 | 135842-82-9 | 112721-05-8 | 111115-85-6 | 122543-26-4 |
| 122543-27-5 | 114101-59-6 | 113148-32-6 | 113148-33-7 | 130068-19-8 | 130068-22-3 | 113148-34-8 |
| 113148-35-9 | 122932-71-2 | 130068-23-4 | 122932-67-6 | 122932-68-7 | 130068-24-5 | 130068-20-1 |
| 122932-13-2 | 122932-65-4 | 130068-21-2 | 122932-66-5 | 134012-65-0 | 122932-69-8 | 122932-70-1 |
| 122932-14-3 | 105932-79-4 | 105932-80-7 | 114511-94-3 | 113477-91-1 | 107460-03-7 | 107460-04-8 |
| 111590-22-8 | 111590-23-9 | 122190-99-2 | 123422-99-1 | 130300-83-3 | 117101-87-8 | 117101-88-9 |
| 114732-46-6 | 114732-47-7 | 92354-84-2 | 117101-89-0 | 106440-47-5 | 106440-48-6 | 121853-30-3 |
| 121853-32-5 | 121853-31-4 | 121853-33-6 | 98513-08-7 | 121683-20-3 | 121683-21-4 | 111069-31-9 |
| 111069-32-0 | 133064-07-0 | 119939-20-7 | 119939-21-8 | 117848-74-5 | 117848-75-6 | 135622-99-0 |
| 135623-00-6 | 116917-64-7 | 116917-65-8 | 136331-40-3 | 136331-39-0 | 126546-29-0 | 126546-28-9 |
| 126546-30-3 | 135494-18-7 | 135494-16-5 | 135494-14-3 | 117848-76-7 | 117848-77-8 | 118216-07-2 |
| 117742-07-1 | 117742-08-2 | 128087-24-1 | 122071-92-5 | 117871-32-6 | 123242-64-8 | 123242-65-9 |
| 123338-22-7 | 123338-23-8 | 133556-83-9 | 128027-12-3 | 126966-95-8 | 136697-02-4 | 111115-86-7 |
| 111115-87-8 | 128511-35-3 | 128511-36-4 | 130588-15-7 | 130588-16-8 | 120945-90-6 | 120945-91-7 |
| 120945-92-8 | 120945-93-9 | 136895-55-8 | 136895-56-9 | 121938-24-7 | 136107-95-4 | 120843-52-6 |
| 133837-03-3 | 128558-11-2 | 133837-04-4 | 128558-12-3 | 129403-74-3 | 135844-45-0 | 129403-75-4 |
| 135844-46-1 | 128558-10-1 | 133837-05-5 | 133837-06-6 | 135526-95-3 | 129736-20-5 | 136045-54-0 |
| 136045-55-1 | 136045-57-3 | 136045-56-2 | 136045-58-4 | 128558-13-4 | 128558-14-5 | 128769-09-5 |
| 128769-10-8 | 114733-35-6 | 114733-36-7 | 115902-35-7 | 115902-36-8 | 128171-90-4 | 133134-58-4 |
| 133134-59-5 | 131461-73-9 | 95471-36-6 | 95471-37-7 | 126904-31-2 | 126904-32-3 | 133134-60-8 |
| 133134-61-9 | 128664-24-4 | 122191-00-8 | 128664-16-4 | 102523-99-9 | 113741-78-9 | 113741-79-0 |
| 137467-88-0 | 132867-11-9 | 121938-25-8 | 102786-08-3 | 98724-98-2 | 106440-49-7 | 106440-50-0 |
| 93051-58-2 | 121938-27-0 | 111642-49-0 | 137467-89-1 | 137467-91-5 | 102347-16-0 | 111069-33-1 |
| 111069-34-2 | 121396-49-4 | 121396-50-7 | 99283-06-4 | 99283-07-5 | 130298-87-2 | 130298-88-3 |
| 126096-82-0 | 121938-26-9 | 114844-81-4 | 137467-74-4 | 137467-92-6 | 120147-25-3 | 120147-22-0 |
| 113741-80-3 | 113741-81-4 | 120147-26-4 | 120147-27-5 | 120147-23-1 | 120147-24-2 | 127314-54-9 |
| 125358-60-3 | 128558-15-6 | 135494-15-4 | 135494-13-2 | 135494-10-9 | 135494-08-5 | 135494-20-1 |
| 135494-09-6 | 135494-03-0 | 135494-07-4 | 135494-17-6 | 135494-05-2 | 135494-02-9 | 135494-06-3 |
| 135494-21-2 | 135494-04-1 | 135494-22-3 | 110734-89-9 | 110734-90-2 | 129736-21-6 | 136797-04-1 |
| 116978-04-2 | 123938-63-6 | 123938-64-7 | 133064-08-1 | 134547-82-3 | 127137-45-5 | 127137-46-6 |
| 130809-12-0 | 133533-78-5 | 133533-79-6 | 114844-82-5 | 114844-83-6 | 135621-63-5 | 127736-40-7 |
| 132965-94-7 | 115038-15-8 | 115038-16-9 | 122961-48-2 | 123896-17-3 | 136394-46-2 | 120037-24-1 |
| 115003-67-3 | 115003-68-4 | 128794-24-1 | 128794-25-2 | 106602-02-2 | 116917-66-9 | 116917-67-0 |
| 126546-314 | 126546-32-5 | 128794-27-4 | 122390-63-0 | 128558-16-7 | 128558-17-8 | 122247-59-0 |
| 122247-60-3 | 129429-40-9 | 127712-27-0 | 129406-07-1 | 129406-08-2 | 129406-09-3 | 128393-18-0 |
| 128393-17-9 | 122191-02-0 | 112263-00-0 | 112263-01-1 | 123780-39-2 | 121015-36-6 | 114844-62-1 |
| 114844-63-2 | 123780-40-5 | 130237-65-9 | 130237-66-0 | 130237-67-1 | 130237-69-3 | 130237-68-2 |
| 125478-95-7 | 108251-10-1 | 115628-09-6 | 115628-10-9 | 114470-77-8 | 114470-76-7 | 125199-79-3 |
| 130427-67-7 | 125478-94-6 | 124757-15-9 | 124757-17-1 | 124757-16-0 | 125478-89-9 | 120177-71-1 |
| 120177-72-2 | 120366-55-4 | 120366-10-1 | 134034-37-0 | 134034-38-1 | 111644-33-8 | 137086-84-1 |
| 131464-10-3 | 131464-11-4 | 132049-94-6 | 132049-96-8 | 131464-12-5 | 131464-13-6 | 132049-95-7 |
| 132049-97-9 | 134496-65-4 | 134496-66-5 | 134496-67-6 | 134496-68-7 | 128634-83-3 | 136108-05-9 |
| 118440-43-0 | 129130-34-3 | 129130-35-4 | 135844-47-2 | 130237-70-6 | 130237-71-7 | 134688-70-3 |
| 134192-94-2 | 124228-55-3 | 124228-54-2 | 128558-18-9 | 130500-92-4 | 130588-18-0 | 118547-75-4 |
| 135976-28-2 | 130588-17-9 | 118547-76-5 | 135976-27-1 | 115038-17-0 | 109189-96-0 | 109189-97-1 |
| 104646-03-9 | 111212-50-1 | 111212-51-2 | 113148-36-0 | 113148-37-1 | 112956-10-2 | 112956-11-3 |
| 130002-85-6 | 130002-84-5 | 128664-35-7 | 95725-99-8 | 95726-00-4 | 110908-55-9 | 129068-97-9 |
| 129068-98-0 | 123512-39-0 | 123512-40-3 | 128171-91-5 | 123512-37-8 | 123512-38-9 | 128171-92-6 |
| 123512-35-6 | 123512-36-7 | 128171-93-7 | 128171-94-8 | 122878-38-0 | 122878-39-1 | 133312-04-6 |
| 133312-05-7 | 130427-68-8 | 130427-69-9 | 124670-02-6 | 124670-03-7 | 125385-28-6 | 135990-72-6 |
| 125977-87-9 | 125977-88-0 | 125265-84-1 | 125265-85-2 | 135541-87-6 | 133483-04-2 | 133483-05-3 |
| 133483-06-4 | 133483-07-5 | 115925-51-4 | 123423-00-7 | 122543-28-6 | 118389-57-4 | 118389-58-5 |
| 133423-88-8 | 123778-98-3 | | | | | |
| 138820-02-7 | 138820-03-8 | 137800-09-0 | 137800-10-3 | 139735-60-7 | 139735-58-3 | 138463-87-3 |

TABLE-continued

| | | | | | | |
|---|---|---|---|---|---|---|
| 141639-41-0 | 141639-39-6 | 138757-61-6 | 140698-50-6 | 140698-78-8 | 140698-77-7 | 140698-76-6 |
| 138988-39-3 | 136799-67-2 | 138263-14-6 | 136107-96-5 | 126902-85-0 | 138575-51-6 | 136108-01-5 |
| 136108-03-7 | 128393-14-6 | 141175-60-2 | 137800-12-5 | 137800-11-4 | 138674-46-1 | 141513-56-6 |
| 141513-57-7 | 141639-38-5 | 139947-54-9 | 132188-68-2 | 139947-55-0 | 141639-42-1 | 138820-01-6 |
| 138360-86-8 | 138360-85-7 | 136107-78-3 | 136107-83-0 | 136107-84-1 | 136107-86-3 | 141639-30-7 |
| 136107-87-4 | 138860-41-0 | 136107-97-6 | 136107-98-7 | 136107-99-8 | 136108-02-6 | 136108-00-4 |
| 138263-16-8 | 138263-15-7 | 138673-08-2 | 139381-09-2 | 139381-12-7 | 139381-10-5 | 139381-13-8 |
| 139381-07-0 | 139381-11-6 | 139381-08-1 | 139568-60-8 | 139568-61-9 | 141414-94-0 | 141414-95-1 |
| 140698-60-8 | 140698-61-9 | 140698-65-3 | 138635-39-9 | 138635-40-2 | 140698-70-0 | 140698-72-2 |
| 140698-73-3 | 138756-60-2 | 138756-61-3 | 138756-10-2 | 136756-04-4 | 141348-29-0 | 139246-89-2 |
| 139246-72-3 | 139568-62-0 | 139568-63-1 | 137877-71-5 | 138635-41-3 | 140698-74-4 | 140698-75-5 |
| 140698-63-1 | 140698-64-2 | 140698-71-1 | 138635-42-4 | 138635-43-5 | 141255-20-1 | 138635-48-0 |
| 138635-44-6 | 138635-47-9 | 138635-49-1 | 138635-50-4 | 124363-02-6 | 136797-02-9 | 124363-06-0 |
| 124363-08-2 | 136797-03-0 | 124363-11-7 | 124363-14-0 | 140698-62-0 | 140698-67-5 | 138635-46-8 |
| 140698-69-7 | 140698-59-5 | 140698-66-4 | 140698-68-6 | 121852-88-8 | 140207-71-2 | 138545-05-8 |
| 128002-39-1 | 139947-36-7 | 137951-70-3 | 140114-52-9 | 141466-52-6 | 141466-51-5 | 141466-53-7 |
| 113148-32-6 | 139075-02-8 | 123338-23-8 | 138015-86-8 | 137923-84-3 | 137923-85-4 | 139316-37-3 |
| 139316-40-8 | 139316-38-4 | 139316-41-9 | 139316-39-5 | 139316-42-0 | 138756-62-4 | 137877-72-6 |
| 136797-04-1 | 137800-13-6 | 137800-14-7 | 137923-86-5 | 139947-53-8 | 140877-00-5 | 141050-01-3 |
| 141050-02-4 | 141176-81-0 | 137923-96-7 | 130237-70-6 | 138157-22-9 | 138413-77-1 | 142804-38-4 |
| 142804-39-5 | 143861-51-2 | 144637-02-5 | 144200-36-2 | 142191-71-7 | 144323-16-0 | 144323-19-3 |
| 144323-18-2 | 144323-17-1 | 144323-20-6 | 144133-29-9 | 132654-55-8 | 143241-66-1 | 144198-73-2 |
| 143011-77-2 | 144199-23-5 | 143178-41-0 | 143178-42-1 | 144417-19-5 | 144417-20-9 | 144323-76-2 |
| 144323-79-5 | 144323-72-8 | 144323-74-0 | 144323-73-9 | 144323-75-1 | 144323-70-6 | 144323-71-7 |
| 144133-61-9 | 143241-73-0 | 142539-95-5 | 142539-94-4 | 142931-03-1 | 142931-02-0 | 142900-83-2 |
| 142900-82-1 | 142539-48-8 | 142539-51-3 | 142539-45-5 | 142539-46-6 | 142539-47-7 | 142539-49-9 |
| 143045-10-7 | 144713-62-2 | 144713-63-3 | 143045-34-5 | 143045-35-6 | 132729-32-9 | 142637-20-5 |
| 142637-21-6 | 144714-48-7 | 143198-13-4 | 110734-87-7 | 110734-88-8 | 98845-93-3 | 98845-94-4 |
| 142662-24-6 | 113014-94-1 | 138756-60-2 | 114964-74-8 | 128794-17-2 | 141961-30-0 | 113913-65-8 |
| 113913-67-0 | 135433-10-2 | 143972-41-2 | 144415-57-6 | 141961-69-5 | 136894-51-4 | 133925-44-7 |
| 143011-78-3 | 124362-97-6 | 143846-01-9 | 143845-95-8 | 143845-93-6 | 143846-02-0 | 143845-94-7 |
| 143845-91-4 | 143845-90-3 | 143845-99-2 | 143845-98-1 | 143845-96-9 | 143845-97-0 | |
| 143846-03-1 | 143845-88-9 | 143845-89-0 | 143846-00-8 | 143639-72-9 | 141961-70-8 | 143639-71-8 |
| 143639-70-7 | 126902-81-6 | 116676-85-8 | 123081-70-9 | 142193-21-3 | 142193-22-4 | 144045-54-5 |
| 144045-71-6 | 131359-89-2 | 143221-34-5 | 143221-32-3 | 143221-33-4 | 142191-66-0 | 141910-32-9 |
| 141910-31-8 | 142193-23-5 | 142193-24-6 | 144904-05-2 | 144904-06-3 | 144903-93-5 | |
| 144904-07-4 | 144903-94-6 | 144904-08-5 | 144903-95-7 | 143973-37-9 | 143973-38-0 | 144904-09-6 |
| 144903-96-8 | 144904-10-9 | 144903-97-9 | 144904-11-0 | 144903-98-0 | 144904-13-2 | 144904-00-7 |
| 144904-14-3 | 144904-15-4 | 144904-02-9 | 144904-17-6 | 144904-04-1 | 144904-16-5 | 144904-03-0 |
| 143513-66-0 | 143221-25-4 | 143513-67-1 | 143221-26-5 | 124228-52-0 | 124228-53-1 | 141910-33-0 |
| 141910-34-1 | 141910-35-2 | 141910-36-3 | 143241-69-4 | 143241-70-7 | 144324-65-2 | 144324-64-1 |
| 144324-61-8 | 144324-60-7 | 142462-46-2 | 144132-35-4 | 144132-96-7 | 144132-38-7 | 144132-39-8 |
| 141910-37-4 | 141910-38-5 | 143241-67-2 | 143241-68-3 | 141933-70-2 | 141933-71-3 | 141933-72-4 |
| 141933-73-5 | 131143-43-6 | 140698-38-0 | 140698-47-1 | 140698-78-9 | 138988-32-6 | 144591-26-4 |
| 143241-71-8 | 143241-72-9 | 141910-39-6 | 141910-40-9 | 113148-32-6 | 143298-63-9 | 142931-00-8 |
| 142931-01-9 | 143973-31-3 | 143973-30-2 | 133064-07-0 | 143514-12-5 | 142845-01-0 | 142844-93-7 |
| 142844-97-1 | 142844-94-8 | 142844-98-2 | 142844-95-9 | 142844-99-3 | 142844-96-0 | 142845-00-9 |
| 144518-08-1 | 144518-10-5 | 144518-12-7 | 144518-14-9 | 144518-32-1 | 143751-08-0 | 143751-11-5 |
| 144324-00-5 | 144715-60-6 | 144715-62-8 | 144198-25-4 | 144713-87-1 | 144198-24-3 | 139316-37-3 |
| 139316-40-8 | 139316-38-4 | 139316-41-9 | 139316-39-5 | 139316-42-0 | 144716-22-3 | 144716-24-5 |
| 144716-23-4 | 144716-25-6 | 144716-26-7 | 144716-27-8 | 142661-29-8 | 142539-96-6 | 143011-14-7 |
| 142804-40-8 | 142804-41-9 | 144417-01-6 | 144417-02-7 | 143220-71-7 | 134688-70-3 | 143045-26-7 |
| 143045-09-4 | 144518-24-1 | 144518-26-3 | 144519-28-5 | 144518-30-9 | 144518-18-3 | 144518-20-7 |
| 144518-22-9 | 144518-16-1 | 143945-78-7 | 143845-77-6 | 141961-31-1 | 141961-32-2 | 123778-98-3 |
| 61076-98-0 | | | | | | |
| 137800-09-0 | 146155-06-8 | 146155-13-7 | 146155-10-4 | 146155-08-0 | 146155-16-0 | 139735-60-7 |
| 145560-37-8 | 145560-43-6 | 145560-34-5 | 145560-42-5 | 144815-16-7 | 144815-13-4 | 144518-92-3 |
| 121683-18-9 | 144518-89-5 | 72980-23-5 | 146482-45-3 | 146482-46-4 | 146482-44-2 | 146482-47-5 |
| 145752-11-0 | 145559-54-2 | 145559-55-3 | 145187-41-3 | 145187-86-6 | 146048-65-9 | 146048-67-1 |
| 145539-58-8 | 145539-62-4 | 145539-64-6 | 146313-13-5 | 146103-25-5 | 136361-96-1 | 145111-35-9 |
| 145111-36-0 | 145111-32-6 | 145111-33-7 | 145113-71-9 | 144058-44-6 | 145110-64-1 | 145137-09-3 |
| 145893-40-9 | 145893-42-1 | 145893-41-0 | 147682-11-9 | 147447-46-9 | 145110-56-1 | 132965-93-6 |
| 145559-53-1 | 146047-96-3 | 146048-05-7 | 146048-01-3 | 146047-93-0 | 146047-13-4 | 146047-18-9 |
| 147446-98-8 | 146045-21-8 | 146045-22-9 | 145110-35-6 | 145110-36-7 | 145559-30-4 | 145559-29-1 |
| 136394-39-3 | 136394-36-0 | 147445-84-9 | 145110-17-4 | 146927-35-7 | 145186-90-9 | |
| 145186-91-0 | 147276-15-1 | 147276-16-2 | 138756-60-2 | 138756-61-3 | 145110-25-4 | 145714-80-3 |
| 141961-30-0 | 146149-86-2 | 147571-54-8 | 146209-69-0 | 146209-70-3 | 146927-83-5 | 146927-82-4 |
| 146927-80-2 | 145137-25-3 | 145137-26-4 | 126546-13-2 | 147155-15-5 | 147155-14-4 | 146157-19-9 |
| 146157-15-5 | 145560-26-5 | 145560-27-6 | 146157-18-8 | 146157-14-4 | 145560-19-6 | 145560-16-3 |
| 145560-22-1 | 145894-60-6 | 146157-54-2 | 146157-58-6 | 121852-88-8 | 147571-68-4 | 144417-42-5 |
| 138545-05-8 | 147446-45-5 | 144045-71-6 | 126466-51-1 | 145716-23-0 | 145716-24-1 | 134496-64-3 |
| 142193-23-5 | 142193-24-6 | 146210-01-7 | 146210-00-6 | 147682-20-0 | 146316-61-2 | 146316-60-1 |
| 129817-71-6 | 145112-80-7 | 145112-51-8 | 145186-25-0 | 145186-26-1 | 143241-69-4 | 146927-32-4 |
| 143296-23-5 | 143750-32-7 | 143750-34-9 | 143750-33-8 | 143296-22-4 | 143750-31-6 | 126546-26-7 |
| 145110-01-6 | 145110-02-7 | 142462-46-2 | 147445-57-6 | 123422-97-9 | 146807-79-6 | 146807-78-5 |
| 147153-68-2 | 147153-69-3 | 147153-71-7 | 147153-70-6 | 146927-33-5 | 145186-82-9 | 147445-49-6 |
| 147445-50-9 | 145137-83-3 | 145137-84-4 | 145186-28-3 | 145186-29-4 | 147446-99-9 | 147338-67-8 |
| 147447-00-5 | 144997-26-2 | 144997-27-3 | 144996-46-3 | 144996-47-4 | 145714-73-4 | 145714-72-3 |
| 113148-34-8 | 113148-35-9 | 144417-41-4 | 144417-40-3 | 139872-90-5 | 139872-89-2 | 139872-92-7 |

TABLE-continued

| | | | | | | |
|---|---|---|---|---|---|---|
| 139872-91-6 | 145139-22-6 | 145139-20-4 | 145139-21-5 | 117742-07-1 | 144997-46-6 | 144997-49-9 |
| 145750-63-6 | 147278-86-2 | 147278-88-4 | 147682-43-7 | 142804-40-8 | 145184-76-5 | 142804-41-9 |
| 145184-78-7 | 146047-11-2 | 147153-80-8 | 147153-79-5 | 130237-70-6 | 145559-08-6 | 145559-09-7 |
| 145138-48-3 | 104646-02-8 | 144592-22-3 | 145893-44-3 | 145138-44-9 | 138157-22-9 | 136413-77-1 |
| 146153-83-5 | 146153-85-7 | 146153-84-6 | 147446-27-3 | 147855-79-6 | 147855-78-5 | 147652-65-1 |
| 146315-86-8 | 148733-60-2 | 147573-96-4 | 146315-89-1 | 121683-18-9 | 147573-95-3 | 147573-98-6 |
| 147573-97-5 | 147573-99-7 | 138757-61-6 | 142191-71-7 | 149823-08-5 | 148641-46-7 | 148641-47-8 |
| 118901-31-8 | 148881-74-7 | 148881-75-8 | 148500-47-4 | 143241-73-0 | 127651-24-5 | 147447-46-9 |
| 148155-96-8 | 148155-97-9 | 148155-98-0 | 148155-99-1 | 148156-00-7 | 148156-25-6 | 148155-93-5 |
| 148155-91-3 | 148155-95-7 | 148155-94-6 | 148155-92-4 | 146315-92-6 | 146047-96-3 | 148499-85-8 |
| 147953-63-7 | 146927-35-7 | 148325-02-4 | 148499-87-0 | 149407-22-7 | 138756-60-2 | 148325-18-2 |
| 146705-43-3 | 148500-48-5 | 148500-10-1 | 148790-23-2 | 147339-20-6 | 147339-31-9 | 147339-26-2 |
| 147339-22-8 | 147339-23-9 | 147339-21-7 | 126546-12-1 | 149022-30-0 | 149408-33-3 | 132965-91-4 |
| 147339-39-7 | 147339-28-4 | 147339-35-3 | 148374-10-1 | 148374-09-8 | 148374-11-2 | 147601-65-8 |
| 147601-66-9 | 147601-71-6 | 147601-62-5 | 147601-63-6 | 147601-61-4 | 147601-70-5 | 147601-72-7 |
| 147601-68-1 | 147601-74-9 | 147601-64-7 | 148790-21-0 | 147339-33-1 | 147339-37-5 | 123081-71-0 |
| 149408-05-9 | 139947-36-7 | 148940-39-0 | 148940-40-3 | 131595-94-3 | 149566-80-3 | 146210-01-7 |
| 148501-29-5 | 149957-02-8 | 149957-03-9 | 147478-60-2 | 148499-86-9 | 101962-78-1 | 147979-62-2 |
| 147446-99-9 | 147338-67-8 | 131143-43-6 | 146412-24-0 | 146412-23-9 | 146412-22-8 | 148498-79-7 |
| 146412-25-1 | 146214-58-6 | 146214-52-0 | 146214-54-2 | 146214-55-3 | 146214-56-4 | 146214-53-1 |
| 136894-55-8 | 148734-99-0 | 148735-01-7 | 148735-02-8 | 148735-00-6 | 149566-05-2 | 148995-83-9 |
| 148940-12-9 | 147278-86-2 | 147278-88-4 | 144132-46-7 | 144132-47-8 | 150901-60-3 | 148068-65-9 |
| 135844-47-2 | 147954-46-9 | 130237-70-6 | 148845-93-6 | 133483-04-2 | 133483-06-4 | |
| 143861-51-2 | 86025-40-3 | 140698-77-7 | 110157-83-0 | 119939-22-9 | 149025-02-5 | 146047-13-4 |
| 106640-40-8 | 162063-81-2 | 162995-35-9 | 146047-18-9 | 162002-24-6 | 162568-72-1 | 162393-85-3 |
| 162393-86-4 | 162914-27-4 | 151285-69-7 | 160405-58-3 | 159607-64-4 | 160275-58-1 | 160275-59-2 |
| 159965-10-3 | 159844-29-8 | 162568-68-5 | 153553-90-3 | 161818-29-7 | 161309-25-7 | 162263-95-8 |
| 161818-30-0 | 160275-56-9 | 160275-57-0 | 161026-92-2 | 162568-67-4 | 161414-02-4 | 159966-54-8 |
| 160871-17-0 | 160577-004 | 162077-60-3 | 161247-57-0 | 159576-88-2 | 161736-34-1 | 160185-91-1 |
| 161347-37-1 | 159522-57-3 | 160185-81-9 | 160185-83-1 | 160185-82-0 | 160185-85-3 | 160185-84-2 |
| 160185-86-4 | 160185-87-5 | 163480-17-9 | 159348-39-7 | 159348-32-0 | 159348-38-6 | 159348-37-5 |
| 159348-34-2 | 162569-43-9 | 113608-98-3 | 159575-66-3 | 159575-68-5 | 159575-67-4 | 159575-65-2 |
| 162077-62-5 | 162077-63-6 | 161026-98-8 | 161026-99-9 | 129817-71-6 | 159521-40-1 | 148501-29-5 |
| 162032-87-3 | 162032-89-5 | 162032-88-4 | 162032-90-8 | 162032-91-9 | 162032-92-0 | 162032-94-2 |
| 162032-95-3 | 162032-96-4 | 162032-98-6 | 162032-93-1 | 162032-97-5 | 162032-99-7 | 162629-36-9 |
| 162033-00-3 | 162033-01-4 | 162455-90-5 | 162455-98-3 | 162456-04-4 | 162455-88-1 | 162455-89-2 |
| 162455-97-2 | 162456-03-3 | 162455-74-5 | 162455-85-8 | 162455-92-7 | 162456-00-0 | 162456-06-6 |
| 162455-84-7 | 162455-91-6 | 162455-99-4 | 162456-05-5 | 162455-76-7 | 162458-02-2 | 162455-75-6 |
| 162456-01-1 | 162456-08-8 | 162456-07-7 | 162456-10-2 | 162456-09-9 | 162455-86-9 | 162455-94-9 |
| 162455-93-8 | 162455-96-1 | 162455-77-8 | 162455-87-0 | 162455-95-0 | 162455-78-9 | |
| 162455-80-3 | 162455-79-0 | 162455-81-4 | 162455-82-5 | 149224-09-9 | 162456-12-4 | 162456-11-3 |
| 162456-14-6 | 162456-13-5 | 161414-83-1 | 161414-84-2 | 161414-85-3 | 160227-93-0 | 161415-00-5 |
| 162875-32-3 | 163480-83-9 | 159575-21-0 | 160870-79-1 | 160339-90-2 | 160339-92-4 | 160339-91-3 |
| 162077-61-4 | 163482-34-6 | 160339-93-5 | 161850-11-9 | 162077-64-7 | 160870-88-2 | 161704-96-7 |
| 160871-27-2 | 162876-18-8 | 161026-74-0 | 161347-80-4 | 161347-81-5 | 161347-75-7 | 161347-72-4 |
| 161347-73-5 | 161347-78-0 | 161347-77-9 | 161347-79-1 | 161347-71-3 | 161347-76-8 | 161347-74-6 |
| 162535-81-1 | 102484-07-1 | 162063-98-1 | 161704-90-1 | 160870-87-1 | 161704-91-2 | 162063-90-3 |
| 144132-38-7 | 160829-87-8 | 159575-22-1 | 160870-83-7 | 160870-84-8 | 159994-33-9 | 160870-77-9 |
| 160870-78-0 | 160966-18-7 | 131143-43-6 | 138988-32-6 | 160871-07-8 | 159669-58-6 | 157298-43-6 |
| 157858-32-7 | 162164-29-6 | 157858-33-8 | 157858-34-9 | 163479-70-7 | 157858-31-6 | 162164-30-9 |
| 162952-75-2 | 162952-76-3 | 160872-31-1 | 161172-88-9 | 161704-61-6 | 159075-77-1 | 159075-79-3 |
| 142931-01-9 | 159075-76-0 | 159075-78-2 | 160871-20-5 | 160871-18-1 | 160871-19-2 | 160871-21-6 |
| 160871-22-7 | 160871-23-8 | 162568-70-9 | 162568-71-0 | 161706-45-2 | 156289-38-2 | 160227-94-1 |
| 160227-95-2 | 161347-85-9 | 161347-84-8 | 161347-83-7 | 162063-91-4 | 162063-92-5 | 162063-93-6 |
| 162063-94-7 | 162063-95-8 | 162063-96-9 | 162456-38-4 | 160026-03-9 | 160026-02-8 | 163479-88-7 |
| 161706-52-1 | 163479-64-9 | 160403-10-1 | 161706-51-0 | 161738-85-8 | 122191-00-8 | 160871-06-7 |
| 161414-03-5 | 199965-54-5 | 161310-02-7 | 162033-12-7 | 162064-19-9 | 161347-42-8 | 161348-09-0 |
| 161347-56-4 | 151880-78-3 | 162079-90-5 | 162079-89-2 | 159318-44-2 | 159204-57-6 | 152572-66-9 |
| 160275-60-5 | 160275-61-6 | 160830-98-8 | 120177-71-1 | 146047-11-2 | 160276-29-9 | 160276-30-2 |
| 159522-88-0 | 157091-78-6 | 157091-86-6 | 157091-93-5 | 157091-87-7 | 157091-88-8 | 157091-89-9 |
| 157091-90-2 | 157091-91-3 | 160478-27-3 | 161026-94-4 | 159522-87-9 | 159607-90-6 | 159577-11-4 |
| 162996-08-9 | 138157-22-9 | 156201-48-8 | | | | |

What is claimed is:

1. A method of modifying an antigenic peptide having a known amino acid sequence, comprising replacing more than one, but not all, the amino acids in odd positions, or respectively, in even positions, of the normal or retro sequence of said known amino acid sequence of the antigenic peptide with glycine, and the amino acid other than glycine have L or D configuration.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:

-continued

```
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Ala Gly Leu Gly Ala Gly
1               5

(2) INFORMATION FOR SEQ ID NO:2:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:2:

Ala Asp Leu Asp Ala Arg
1               5

(2) INFORMATION FOR SEQ ID NO:3:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

Gly Asp Gly Asp Gly Arg
1               5
```